(12) United States Patent
Yamada (10) Patent No.: US 10,052,156 B2
(45) Date of Patent: Aug. 21, 2018

(54) MOVING THE CURSOR TO 2D POSITION IN SECOND TOMOGRAPHIC IMAGE CORRESPONDING TO 3D POSITION CORRESPONDING TO 2D POSITION POINTED BY CURSOR IN FIRST TOMOGRAPHIC IMAGE

(71) Applicant: FUJIFILM Corporation, Tokyo (JP)

(72) Inventor: Kenta Yamada, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 399 days.

(21) Appl. No.: 14/834,884

(22) Filed: Aug. 25, 2015

(65) Prior Publication Data

US 2016/0067008 A1    Mar. 10, 2016

(30) Foreign Application Priority Data

Sep. 4, 2014    (JP) ................................. 2014-180129

(51) Int. Cl.
*G06K 9/00* (2006.01)
*A61B 19/00* (2006.01)
*A61B 5/00* (2006.01)

(52) U.S. Cl.
CPC .......... *A61B 19/5225* (2013.01); *A61B 5/743* (2013.01); *A61B 5/7425* (2013.01); *A61B 2019/524* (2013.01); *A61B 2019/5236* (2013.01); *A61B 2019/5276* (2013.01); *A61B 2019/5289* (2013.01)

(58) Field of Classification Search
None
See application file for complete search history.

(56) References Cited

U.S. PATENT DOCUMENTS

| 2002/0015006 A1 | 2/2002 | Suzuki et al. |
| 2008/0112602 A1 | 5/2008 | Azemoto et al. |
| 2013/0002646 A1* | 1/2013 | Lin ...................... G06T 7/0012 345/419 |

FOREIGN PATENT DOCUMENTS

| JP | 2002011000 A | 1/2002 |
| JP | 2008119252 A | 5/2008 |
| JP | 2010-244224 A | 10/2010 |
| JP | 2011-217947 A | 11/2011 |

OTHER PUBLICATIONS

Communication dated Jan. 17, 2017, from the Japanese Patent Office in counterpart application No. 2014-180129.

* cited by examiner

*Primary Examiner* — Atiba O Fitzpatrick
(74) *Attorney, Agent, or Firm* — Sughrue Mion, PLLC (57) ABSTRACT

A first tomographic image of a three-dimensional image is displayed on a display screen, and a cursor to be operated by a user is also displayed in the displayed first tomographic image, and at least one second tomographic image intersecting the first tomographic image at a three-dimensional position in the three-dimensional image corresponding to a two-dimensional position pointed by the cursor in the first tomographic image is also displayed. A user input by a button operation giving an instruction to move the cursor is received. The cursor is moved to a two-dimensional position in one of the at least one second tomographic image corresponding to the three-dimensional position in the three-dimensional image corresponding to the two-dimensional position pointed by the cursor in the first tomographic image.

10 Claims, 8 Drawing Sheets

MOVING THE CURSOR TO 2D POSITION IN SECOND TOMOGRAPHIC IMAGE CORRESPONDING TO 3D POSITION CORRESPONDING TO 2D POSITION POINTED BY CURSOR IN FIRST TOMOGRAPHIC IMAGE

CROSS-REFERENCE TO RELATED APPLICATIONS

The present application claims priority under 35 U.S.C. § 119 to Japanese Patent Application No. 2014-180129 filed on Sep. 4, 2014. The above application is hereby expressly incorporated by reference, in its entirety, into the present application.

BACKGROUND

The present disclosure relates to an image display apparatus, method and program that displays plural tomographic images of a three-dimensional image intersecting each other on a display screen.

In recent years, a three-dimensional image obtained by imaging a region to be examined of a patient is checked or modified by using display of plural tomographic images of the three-dimensional image intersecting each other at a position at which the region was imaged, for example, such as an axial image, a coronal image and a sagittal image (hereafter, referred to as "orthogonal triaxial images").

Japanese Unexamined Patent Publication No. 2011-217947 (Patent Document 1) proposes a method in which when orthogonal triaxial images of a three-dimensional image are displayed, a cursor is displayed at a position in a tomographic image corresponding to a three-dimensional position in the three-dimensional image at which tomographic images intersect each other. The display is changed, every time the cursor is moved by a user input, to orthogonal triaxial images intersecting each other at a position in the three-dimensional image corresponding to the position of the cursor after movement. Therefore, the user can check and modify a region of interest while appropriately changing the slice positions of the tomographic images.

Japanese Unexamined Patent Publication No. 2010-244224 (Patent Document 2) proposes a method in which when an operation, such as modification, is performed on plural images displayed on a display screen while moving a cursor back and forth between them, the cursor is moved to a predetermined position (a center position or the like) in an image that will become active based on a key operation for switching active images. Accordingly, a usage amount of a mouse is reduced, and a burden of operations on users is reduced.

SUMMARY

Figure 9:
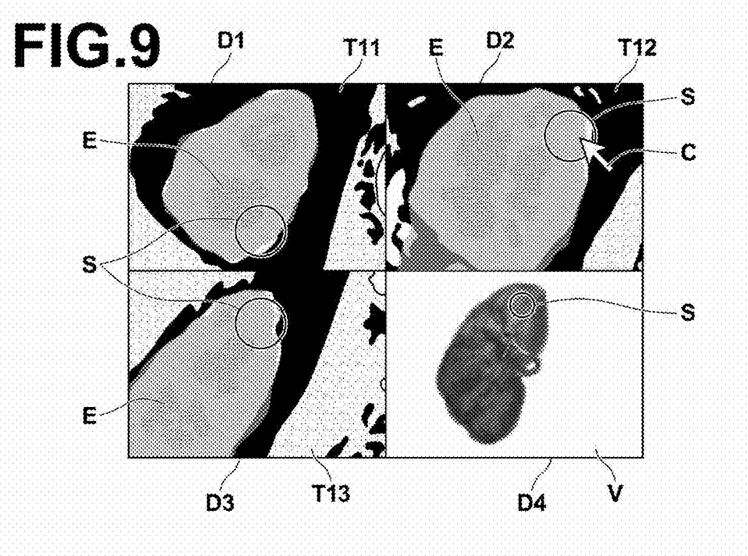
FIG. 9 is a diagram illustrating an example of a display screen displayed by a display control unit.

For example, a case as illustrated in FIG. 9 will be considered. In FIG. 9, a display screen includes four display areas D1 through D4, and three tomographic images T11 through T13, which are orthogonal triaxial images of a three-dimensional image obtained by imaging a kidney region, are displayed in display areas D1 through D3. Further, volume rendering image V of the kidney generated from the three-dimensional image is displayed in display area D4. Further, range E of the kidney region obtained by image analysis or the like is displayed in each of tomographic images T11 through T13. The display is changed, every time cursor C is moved in tomographic images T11 through T13, to display orthogonal triaxial images intersecting each other at a position in the three-dimensional image corresponding to the position of the moved cursor in display areas D1 through D3. Accordingly, a user can check range E of the kidney region, and further modify range E by addition or deletion, if necessary, while appropriately changing slice positions of the tomographic images by moving cursor C by an operation of a mouse or the like. In this case, it is further assumed that when an instruction to modify region E of the kidney region has been given, range S to which modification is applied is further displayed in each of the tomographic images to make it possible to efficiently perform modification on range E of the kidney region. Then, it is possible to perform modification by addition of the region of application range S to range E of the kidney region or by deletion of the region of application range S from range E of the kidney region based on a user input giving an instruction to modify the kidney region by addition or deletion.

Figure 10:
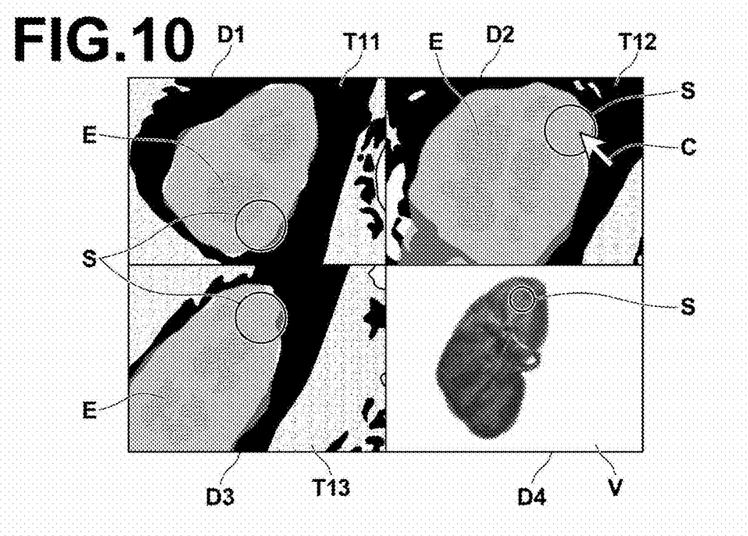
FIG. 10 is a diagram illustrating an example of a display screen after editing, displayed by the display control unit.

Specifically, when the user inputs an instruction to modify by addition while positioning application range S in a part of tomographic image T12 that is not included in range E of the kidney region but shows the kidney on the display screen illustrated in FIG. 9, the region of application range S is added to range E of the kidney region. Consequently, range E of the kidney region on which addition processing has been performed is displayed in each of tomographic images T11 through T13, as illustrated in FIG. 10. However, as illustrated in FIG. 10, a part of range E of the kidney region added by the addition processing is beyond an area showing the kidney in tomographic image T11. Therefore, it is necessary to perform an operation for deleting, from range E of the kidney region, the part beyond the area showing the kidney in the tomographic image T11.

Figure 14:
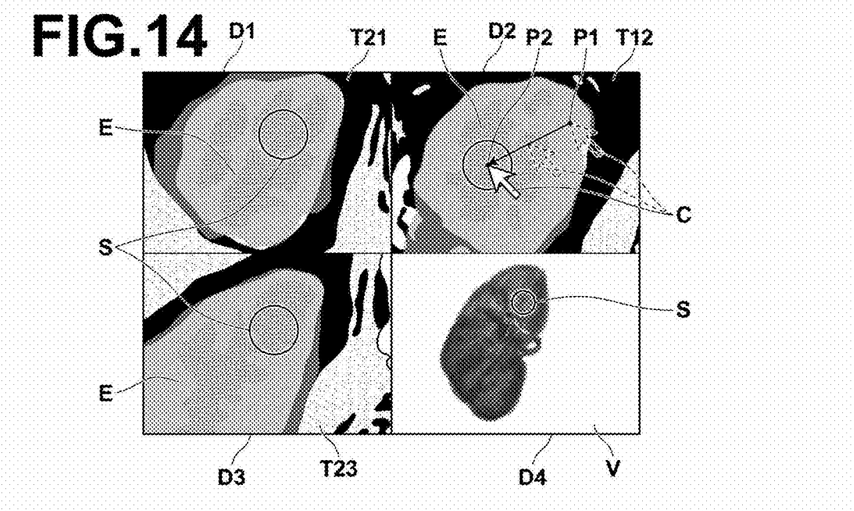
FIG. 14 is a diagram for explaining a problem to be solved by the disclosure.

At that time, if the user operates a mouse and directly moves cursor C located in display area D2 toward display area D1 for example as illustrated in FIG. 14, the slice positions of tomographic images displayed in display areas D1 and D3 change synchronously with the movement of cursor C. Therefore, after the user moves cursor C to display area D1, the user further needs to find and display tomographic image T11 that was displayed before the slice position was changed, and to move cursor C from the current position to a position necessary to perform a modification operation in tomographic image T11. Such complicated operations are required, and there is a problem that operation characteristics are low. Meanwhile, FIG. 14 illustrates a state in which an image displayed in display area D1 has been switched from tomographic image T11 (z=z1) to tomographic image T21 (z=z2), and an image displayed in display area D3 has been switched from tomographic image T13 (y=y1) to tomographic image T23 (y=y2) by movement of cursor C from coordinate P1 (y1, z1) to coordinate P2 (y2, z2) in tomographic image T12 (x=x1).

Further, instead of directly moving cursor C by an operation of a mouse, when cursor C is moved from tomographic image T12 to a predetermined position (a center position or the like) in tomographic image T11 based on a key operation by using the method disclosed in Patent Document 2, a user also needs to further perform an operation of moving cursor C from the current position to a position necessary to perform a modification operation in tomographic image T11 after cursor C is moved to tomographic image T11 by the key operation. Therefore, there is a problem that operation characteristics are low.

In view of the foregoing circumstances, the present disclosure provides an image display apparatus, method and program that can improve the efficiency of operations of checking or modifying a three-dimensional image while moving a cursor back and forth between plural tomographic images of the three-dimensional image intersecting each other, and which are displayed on a display screen.

An image display apparatus of the present disclosure includes a display control unit that displays a first tomographic image of a three-dimensional image on a display screen, and also displays a cursor to be operated by a user in the displayed first tomographic image, and also displays at least one second tomographic image intersecting the first tomographic image at a three-dimensional position in the three-dimensional image corresponding to a two-dimensional position pointed by the cursor in the first tomographic image, an operation receiving unit that receives a user input by a button operation giving an instruction to move the cursor, and a cursor control unit that moves, in response to receipt of the user input by the button operation at the operation receiving unit, the cursor to a two-dimensional position in one of the at least one second tomographic image corresponding to the three-dimensional position in the three-dimensional image corresponding to the two-dimensional position pointed by the cursor in the first tomographic image.

Here, the expression "a three-dimensional position in the three-dimensional image corresponding to a two-dimensional position in the tomographic image" means a three-dimensional position of a voxel in a three-dimensional image represented by a pixel at a two-dimensional position in the tomographic image.

Further, specific examples of "a button operation" are a button operation by a left button or a right button of a mouse, a button (key) operation on a keyboard, an operation of moving a center button (wheel button) of the mouse forward and backward, and the like.

The image display apparatus of the present disclosure may further include an edit processing unit that changes, in response to a user input giving an instruction to perform edit, image information about a partial region of the three-dimensional image including the three-dimensional position in the three-dimensional image corresponding to the two-dimensional position pointed by the cursor in the first tomographic image or one of the at least one second tomographic image in which the cursor is displayed or information related to each of voxels in the partial region other than the image information.

Here, specific examples of "a partial region of the three-dimensional image including the three-dimensional position in the three-dimensional image corresponding to the two-dimensional position pointed by the cursor" are a spherical region having a predetermined radius, a rectangular parallelepiped or polyhedral region having a predetermined size and the like with their centers located at the three-dimensional position in the three-dimensional image corresponding to the two-dimensional position pointed by the cursor.

In the image display apparatus of the present disclosure, when a region of interest has been set in the three-dimensional image, the display control unit may display the range of the set region of interest in the first tomographic image and the at least one second tomographic image displayed on the display screen in a visually recognizable manner. Further, the edit processing unit may change, in response to the user input giving an instruction to perform edit, information that is related to each of the voxels in the partial region and represents whether each of the voxels in the partial region is included in the region of interest.

At this time, for example, the edit processing unit may change all information representing whether each of voxels in the partial region is included in the region of interest, and which is related to each of the voxels in the partial region, to information representing that each of the voxels is included in the region of interest. Alternatively, the edit processing unit may change all information representing whether each of the voxels in the partial region is included in the region of interest, and which is related to each of the voxels in the partial region, to information representing that each of the voxels is not included in the region of interest.

Further, specific examples of a mode of "displaying the range of the region of interest in a visually recognizable manner" are a mode of displaying the region of interest in a color or colors different from the other regions, a mode of displaying a surrounding line around the region of interest, and the like.

In the image display apparatus of the present disclosure, the display control unit may display plural second tomographic images, and the operation receiving unit may receive at least two different button operations. Further, the cursor control unit may determine, based on which of the at least two different button operation has been performed, one of the plurality of the second tomographic images into which the cursor is moved.

For example, the operation receiving unit may receive operations of at least two different arrow keys on a keyboard, and the cursor control unit may move a cursor from the first tomographic image in which the cursor is currently located into a second tomographic image located in the direction indicated by the operated arrow key or keys. At this time, when two or more second tomographic images are present toward the direction indicated by the operated arrow key or keys, the cursor control unit should move the cursor into one of the second tomographic images selected based on a predetermined rule.

An image display method of the present disclosure includes the step of displaying a first tomographic image of a three-dimensional image on a display screen, and also displaying a cursor to be operated by a user in the displayed first tomographic image, and also displaying at least one second tomographic image intersecting the first tomographic image at a three-dimensional position in the three-dimensional image corresponding to a two-dimensional position pointed by the cursor in the first tomographic image, the step of receiving a user input by a button operation giving an instruction to move the cursor, and the step of moving, in response to receipt of the user input by the button operation, the cursor to a two-dimensional position in one of the at least one second tomographic image corresponding to the three-dimensional position in the three-dimensional image corresponding to the two-dimensional position pointed by the cursor in the first tomographic image.

The image display method of the present disclosure may further include the step of changing, in response to a user input giving an instruction to perform edit, image information about a partial region of the three-dimensional image including the three-dimensional position in the three-dimensional image corresponding to the two-dimensional position pointed by the cursor in the first tomographic image or one of the at least one second tomographic image in which the cursor is displayed or information related to each of voxels in the partial region other than the image information, and the step of displaying, on the display screen, plural tomographic images of the three-dimensional image in which one of the image information and the information other than the image information has been changed, and the plural tomographic images intersecting each other at the three-dimensional position in the three-dimensional image corresponding to the two-dimensional position pointed by the cursor.

A non-transitory computer-readable recording medium of the present disclosure stores therein an image display program that causes a computer to function as a display control unit that displays a first tomographic image of a three-dimensional image on a display screen, and also displays a cursor to be operated by a user in the displayed first tomographic image, and also displays at least one second tomographic image intersecting the first tomographic image at a three-dimensional position in the three-dimensional image corresponding to a two-dimensional position pointed by the cursor in the first tomographic image, an operation receiving unit that receives a user input by a button operation giving an instruction to move the cursor, and a cursor control unit that moves, in response to receipt of the user input by the button operation at the operation receiving unit, the cursor to a two-dimensional position in one of the at least one second tomographic image corresponding to the three-dimensional position in the three-dimensional image corresponding to the two-dimensional position pointed by the cursor in the first tomographic image.

The non-transitory computer-readable recording medium may store therein the image display program that causes a computer to function further as an edit processing unit that changes, in response to a user input giving an instruction to perform edit, image information about a partial region of the three-dimensional image including the three-dimensional position in the three-dimensional image corresponding to the two-dimensional position pointed by the cursor in the first tomographic image or one of the at least one second tomographic image in which the cursor is displayed or information related to each of voxels in the partial region other than the image information.

The image display program of the present disclosure normally includes plural program modules, and the function of each of the aforementioned units is achieved by one or plural program modules. These program module groups are recorded in a recording medium, such as a CD-ROM and a DVD, or recorded in a storage attached to a server computer or a network storage in a downloadable manner, and provided for users.

According to the image display apparatus, method and program of the present disclosure, a first tomographic image of a three-dimensional image is displayed on a display screen, and a cursor to be operated by a user is also displayed in the displayed first tomographic image, and at least one second tomographic image intersecting the first tomographic image at the three-dimensional position in the three-dimensional image corresponding to a two-dimensional position pointed by the cursor in the first tomographic image is also displayed. Further, a user input by a button operation giving an instruction to move the cursor is received. Further, the cursor is moved, only by a simple button operation, to a two-dimensional position in one of the at least one second tomographic image corresponding to the three-dimensional position in the three-dimensional image corresponding to the two-dimensional position pointed by the cursor in the first tomographic image. Therefore, a user can continue to perform an operation of checking, modifying or the like in another tomographic image. Hence, it is possible to more efficiently perform an operation of checking or modifying the three-dimensional image while moving a cursor back and forth between plural tomographic images of the three-dimensional image intersecting each other.

DESCRIPTION OF THE PREFERRED EMBODIMENTS

Figure 1:
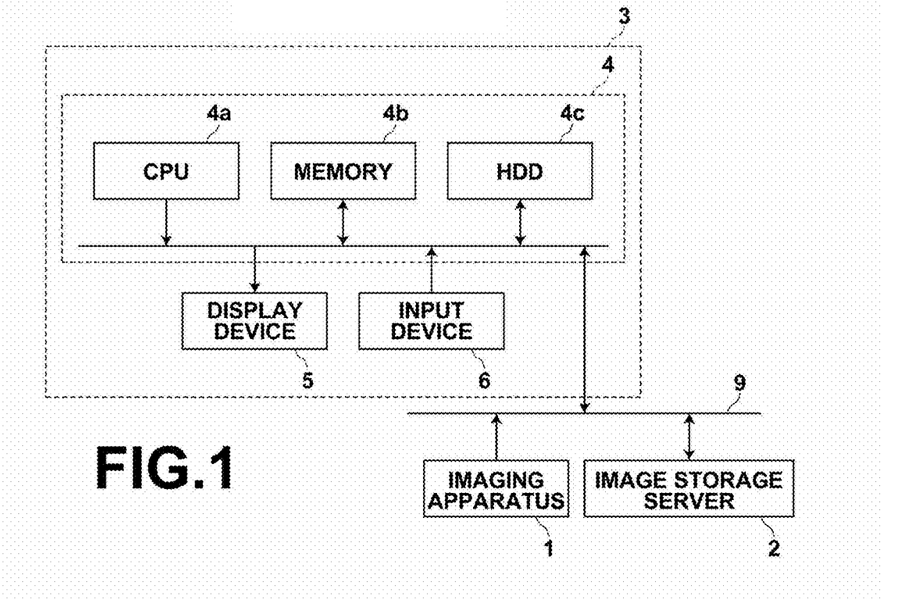
FIG. 1 is a schematic diagram illustrating the configuration of an image processing system including a first embodiment of the present disclosure.

Hereinafter, a first embodiment of the present disclosure will be described with reference to drawings. FIG. 1 is a schematic block diagram illustrating the configuration of an image processing system including the first embodiment of the present disclosure. As illustrated in FIG. 1, this system includes an imaging apparatus 1, an image storage server 2 and an image display apparatus 3 according to the first embodiment of the present disclosure connected to each other through a network 9 in such a manner that they can communicate with each other.

The imaging apparatus 1 performs imaging on a region to be examined of a patient, and generates three-dimensional image data (a three-dimensional image) representing the region based on information obtained by imaging. The imaging apparatus 1 stores and outputs the three-dimensional image data, as a file based on DICOM (Digital Imaging and Communication in Medicine) standard. Specifically, the imaging apparatus 1 is a CT (Computed Tomography) apparatus, an MSCT (Multi Slice CT) apparatus, an MRI (Magnetic Resonance Imaging) apparatus, a PET (positron emission tomography) apparatus, a US (Ultrasonograph) apparatus and the like.

The image storage server 2 is a computer that stores an image obtained by the imaging apparatus 1 in a database, and manages the image. The image storage server 2 retrieves an image from the database based on a request for retrieval of the image sent from the image display apparatus 3, and sends the extracted image to the image display apparatus 3. The image storage server 2 includes a storage unit in which the database is configured and database management software.

The image display apparatus 3 is a computer that obtains an image from the imaging apparatus 1 or the image storage server 2 based on a request by a user, and displays the image. The image display apparatus 3 includes an apparatus main body 4 in which a CPU and the like are stored, a display device 5, such as a display, and an input device 6, such as a mouse and a keyboard.

The input device 6 corresponds to an operation receiving unit of the present disclosure. The input device 6 receives a user input giving an instruction to move a cursor or the like. In the embodiment of the present disclosure, the input device 6 is assumed to include both of a mouse and a keyboard, and to receive a user input by movement of the mouse itself, as a user input giving an instruction to move a cursor based on a movement direction and a movement amount of the mouse, and to receive an operation of an arrow key (a button unit) on the keyboard, as a user input giving an instruction to move the cursor from the display image in which the cursor is currently located into another display image located in the direction indicated by the operated arrow key.

The apparatus main body 4 includes a CPU (Central Processing Unit) 4a, a memory 4b and an HDD (Hard Disk Drive) 4c. The CPU 4a, the memory 4b and the HDD 4c are connected to each other through a bus line. The HDD 4c stores various programs including the image display program of the present disclosure and data referred to by the programs. The CPU 4a performs various kinds of control processing and operation processing based on the programs stored in HDD 4c by using the memory 4b, as a temporary storage area.

Figure 2:
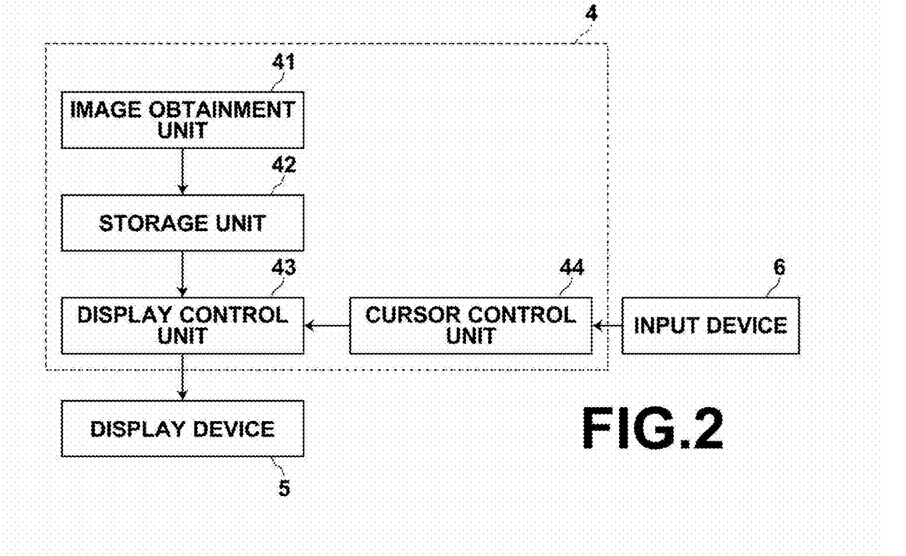
FIG. 2 is a block diagram illustrating functions installed in an image display apparatus illustrated in FIG. 1.

FIG. 2 is a functional block diagram illustrating the function of the image display apparatus 3. As illustrated in FIG. 2, the apparatus main body 4 of the image display apparatus 3 functions as an image obtainment unit 41, a display control unit 43 and a cursor control unit 44 by performance of information processing by the CPU 4a using the programs stored in the HDD 4c. Further, the memory 4b and the HDD 4c function as a storage unit 42.

The image obtainment unit 41 obtains an image from the imaging apparatus 1 or the image storage server 2 based on a request by a user. For example, the image obtainment unit 41 receives a user input giving an instruction to display a three-dimensional image, and in which the three-dimensional image is specified, and obtains the specified three-dimensional image from the imaging apparatus 1 or the image storage server 2. The image obtained by the image obtainment unit 41 is stored in the storage unit 42.

Figure 3:
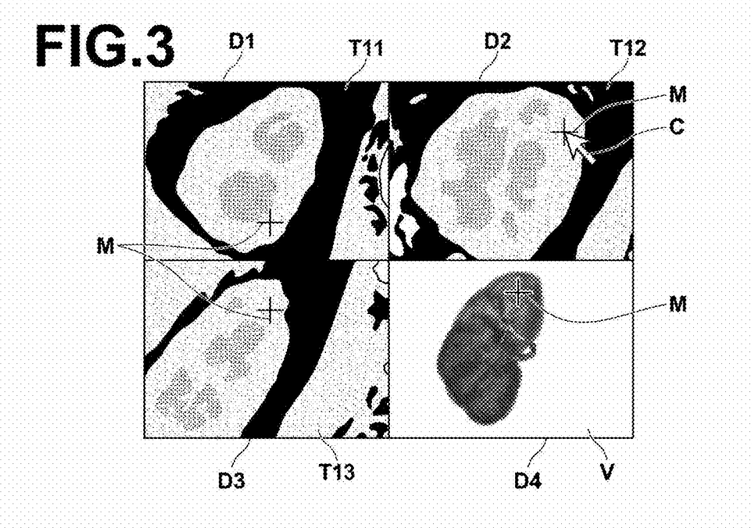
FIG. 3 is a diagram illustrating an example of a display screen displayed by a display control unit.

The display control unit 43 reads out, from the storage unit 42, the three-dimensional image an instruction of display of which has been given, and displays plural tomographic images of the three-dimensional image intersecting each other on a display screen of the display device 5. For example, the display control unit 43 reads out a three-dimensional image obtained by imaging a kidney region, and an instruction of display of which has been given, from the storage unit 42. Further, as illustrated in FIG. 3, three tomographic images T11 through T13, which are orthogonal triaxial images of the three-dimensional image, are displayed in display areas D1 through D3 on a display screen including four display areas D1 through D4. Volume rendering image V of the kidney generated from the three-dimensional image is displayed in display area D4.

Further, the display control unit 43 displays, in one of tomographic images T11 through T13, cursor C at a position corresponding to a three-dimensional position at which three tomographic images T11 through T13 intersect each other in the three-dimensional image. Further, the display control unit 43 displays, in each of tomographic images T11 through T13 and volume rendering image V, cross mark M representing the three-dimensional position in the three-dimensional image at which three tomographic images T11 through T13 intersect each other.

Further, the cursor control unit 44 moves, in response to receipt of a user input of moving the mouse itself at the input device 6, cursor C based on the movement direction and the movement amount of the mouse. Then, the display control unit 43 displays, in display areas D1 through D3, orthogonal triaxial images intersecting each other at the three-dimensional position in the three-dimensional image corresponding to the position of the moved cursor. In this case, display of a tomographic image in at least one of display areas D1 through D3 is changed to another tomographic image at a different slice position.

The cursor control unit 44 moves, in response to receipt of a user input giving an instruction to move cursor C at the input device 6, cursor C based on the instruction by the user input. As described above, the cursor control unit 44 moves, in response to receipt of the user input of moving the mouse itself at the input device 6, cursor C based on the movement direction and the movement amount of the mouse. Further, the cursor control unit 44 moves, in response to receipt of an operation of an arrow key (a button unit) on the keyboard at the input device 6, cursor C from the tomographic image in which cursor C is currently located into another tomographic image located in the direction indicated by the operated arrow key. At this time, the cursor control unit 44 moves cursor C to a two-dimensional position in the tomographic image in which cursor C will be located after movement, and the two-dimensional position corresponding to the three-dimensional position in the three-dimensional image corresponding to the two-dimensional position pointed by cursor C in the tomographic image in which cursor C was located before movement. In this case, the three-dimensional position corresponding to the position of the cursor in the three-dimensional image does not change. Therefore, the display of a tomographic image in none of display areas D1 through D3 is changed to another tomographic image at a different slice position.

Figure 4:
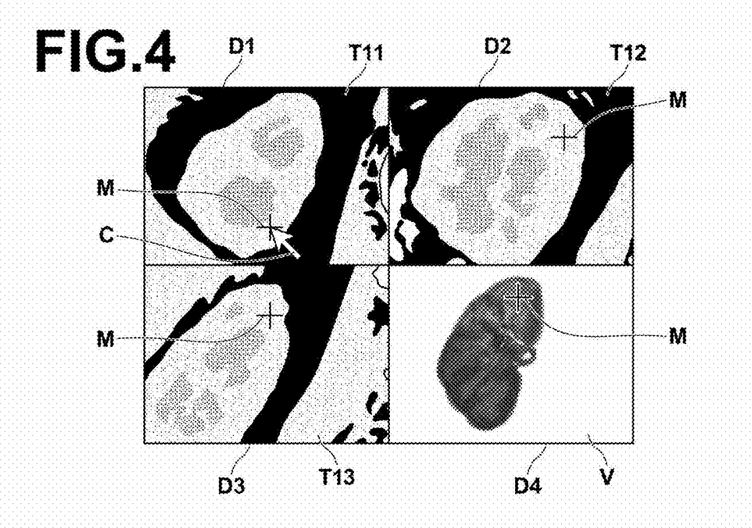
FIG. 4 is a diagram for explaining movement of a cursor by a button operation (No. 1)
Figure 5:
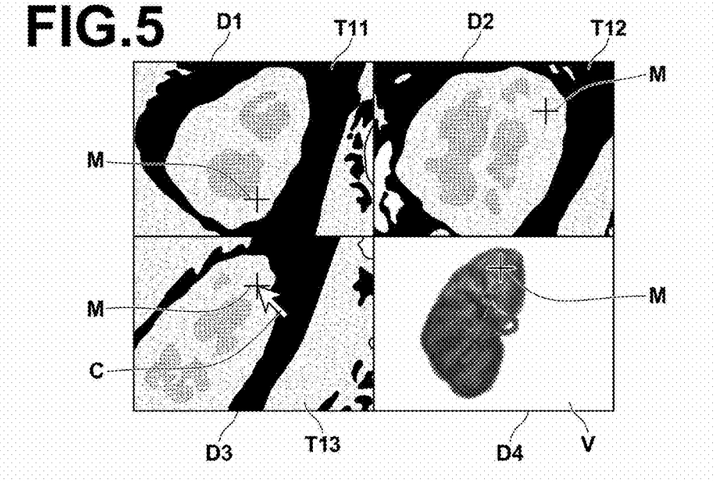
FIG. 5 is a diagram for explaining movement of a cursor by a button operation (No. 2)

For example, when a left arrow key on a keyboard is operated while cursor C is located in tomographic image T12, as illustrated in FIG. 3, the cursor control unit 44 moves cursor C to a two-dimensional position in tomographic image T11 (a position at which cross mark M is displayed in tomographic image T11), as illustrated in FIG. 4. The two-dimensional position in tomographic image T11, which is located to the left of tomographic image T12, corresponds to the three-dimensional position in the three-dimensional image corresponding to the two-dimensional position pointed by cursor C in tomographic image T12, in which cursor C was located before movement. After then, when a down arrow key on the keyboard is further operated, the cursor control unit 44 moves cursor C to a two-dimensional position in tomographic image T13 (a position at which cross mark M is displayed in tomographic image T13), as illustrated in FIG. 5. The two-dimensional position in tomographic image T13, which is located under tomographic image T11, corresponds to the three-dimensional position in the three-dimensional image corresponding to the two-dimensional position pointed by cursor C in tomographic image T11, in which cursor C was located before movement.

Figure 6:
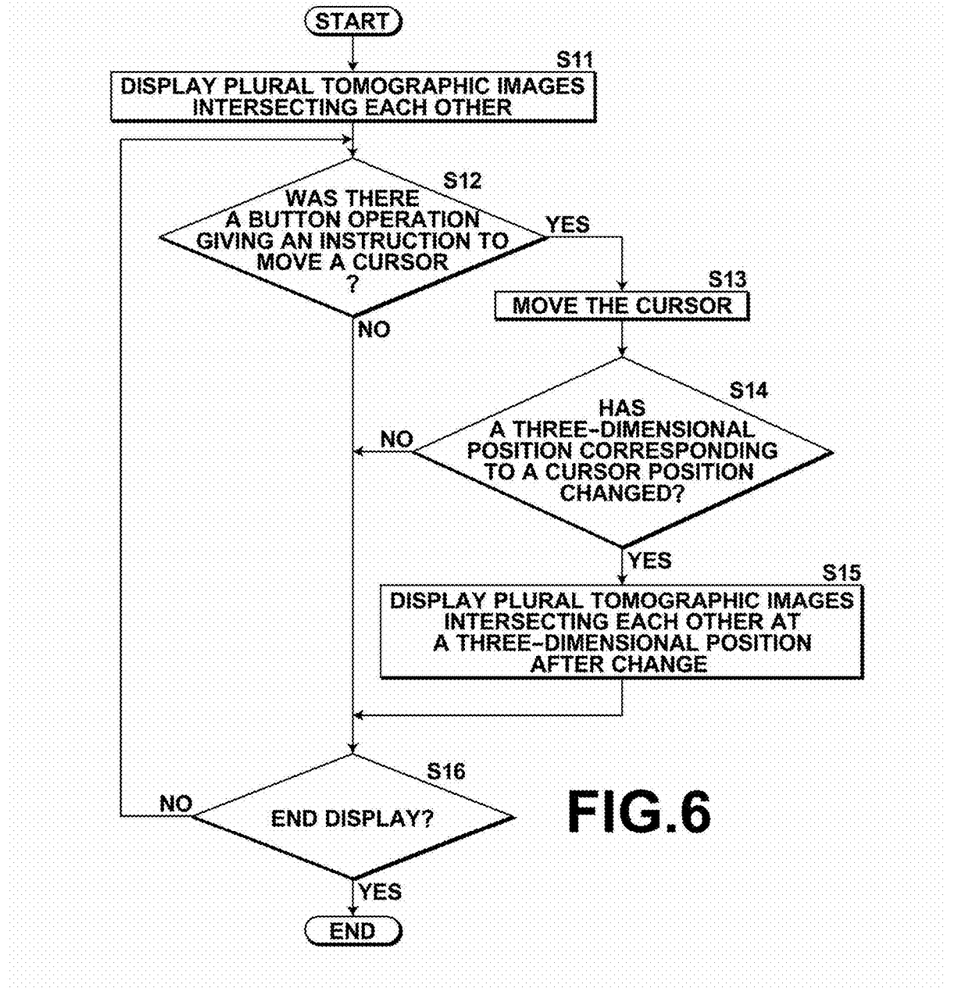
FIG. 6 is a flow chart showing a flow of processing performed by the image display apparatus.

Next, a flow of processing performed by the image display apparatus 3 will be described with reference to a flow chart illustrated in FIG. 6. First, the image display apparatus 3 receives a user input giving an instruction to display a three-dimensional image, and in which the three-dimensional image is specified. Then, the image obtainment unit 41 obtains the specified three-dimensional image from the imaging apparatus 1 or the image storage server 2. The display control unit 43 displays plural tomographic images intersecting each other of the three-dimensional image, an instruction of display of which has been given, on a display screen of the display device 5 (S11). Then, judgment is made as to whether there was a user input giving an instruction to move the cursor at the input device 6 (S12). If it is judged that there was no user input giving an instruction to move cursor C (S12: NO), judgment is further made as to whether there was an instruction to end display (S16). If it is judged that there was an instruction to end display (S16: YES), processing ends. In contrast, if it is judged that there was no instruction to end display (S16: NO), processing returns to step S12.

Meanwhile, if it is judged that there was a user input giving an instruction to move cursor C (S12: YES), the cursor control unit 44 moves cursor C based on the instruction given by the user input (S13). At this time, if the user input received in step S12 is a user input by movement of a mouse itself, the cursor control unit 44 moves cursor C based on a movement direction and a movement amount of the mouse. If the user input received in step S12 is a user input by operation of an arrow key on the keyboard, the cursor control unit 44 moves cursor C from the tomographic image in which cursor C is currently located into another tomographic image located in a direction indicated by the operated arrow key. Especially, when the cursor control unit 44 moves cursor C based on the user input by operation of an arrow key, the cursor control unit 44 moves cursor C to a two-dimensional position in a tomographic image in which cursor C will be located after movement, and the two-dimensional position corresponding to the three-dimensional position in the three-dimensional image corresponding to the two-dimensional position pointed by cursor C in the tomographic image in which cursor C was located before movement.

Next, the display control unit 43 judges whether the three-dimensional position in the three-dimensional image corresponding to a cursor position has changed by movement of the cursor, in other words (S14). If it is judged that the three-dimensional position has not changed (S14: NO), processing goes to step 16. In contrast, if it is judged that the three-dimensional position has changed in step S14 (S14: YES), the display control unit 43 displays plural tomographic images intersecting each other at a three-dimensional position in the three-dimensional image corresponding the position of the moved cursor on the display screen of the display device 5 (S15). In this case, at least one of tomographic images displayed on the display screen is changed to another tomographic image sliced at a different slice position. Then, processing goes to step S16, and judgment is made as to whether there was an instruction to end display (S16). Then, if it is judged that there was no instruction to end display as described above (S16: NO), processing returns to step S12. In contrast, if it is judged that there was an instruction to end display (S16: YES), processing ends.

As the image display apparatus 3 according to an embodiment of the present disclosure is configured as described above, the display control unit 43 displays a first tomographic image (tomographic image T12) of the three-dimensional image on the display screen, and also displays cursor C to be operated by a user in the displayed first tomographic image (tomographic image T12), and also displays at least one second tomographic image (tomographic images T11 and T13) intersecting the first tomographic image (tomographic image T12) at the three-dimensional position in the three-dimensional image corresponding to the two-dimensional position pointed by cursor C in the first tomographic image (tomographic image T12). Further, the input device 6 (operation receiving unit) receives a user input by a button operation (an operation of an arrow key on the keyboard) giving an instruction to move cursor C. Further, the cursor control unit 44 moves cursor C, only by a simple button operation, to a two-dimensional position in one of the second tomographic images (tomographic image T11 or T13) corresponding to the three-dimensional position in the three-dimensional image corresponding to the two-dimensional position pointed by cursor C in the first tomographic image (tomographic image T12). Therefore, it is possible to perform operations, such as checking and modifying, continuously in another tomographic image. Hence, it is possible to more efficiently perform an operation of checking or modifying the three-dimensional image while moving cursor C back and forth between plural tomographic images of the three-dimensional image intersecting each other.

In the aforementioned embodiment, a case in which the display control unit 43 has a function of displaying, in each of tomographic images T11 through T13 and volume rendering image V, cross mark M representing a three-dimensional position at which three tomographic images T11 through T13 intersect each other in the three-dimensional image was described. However, this function is not always necessary, and the function should be provided, if necessary.

Figure 7:
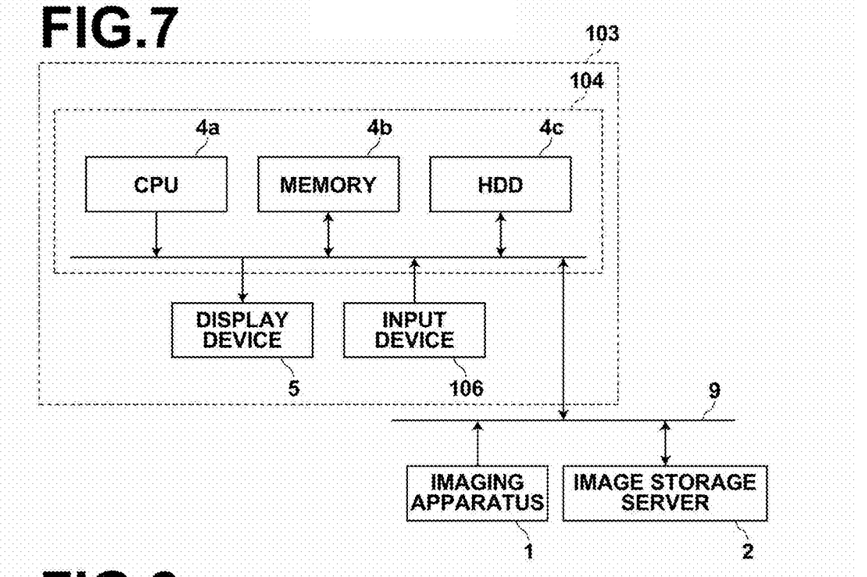
FIG. 7 is a schematic diagram illustrating the configuration of an image processing system including a second embodiment of the present disclosure.
Figure 8:
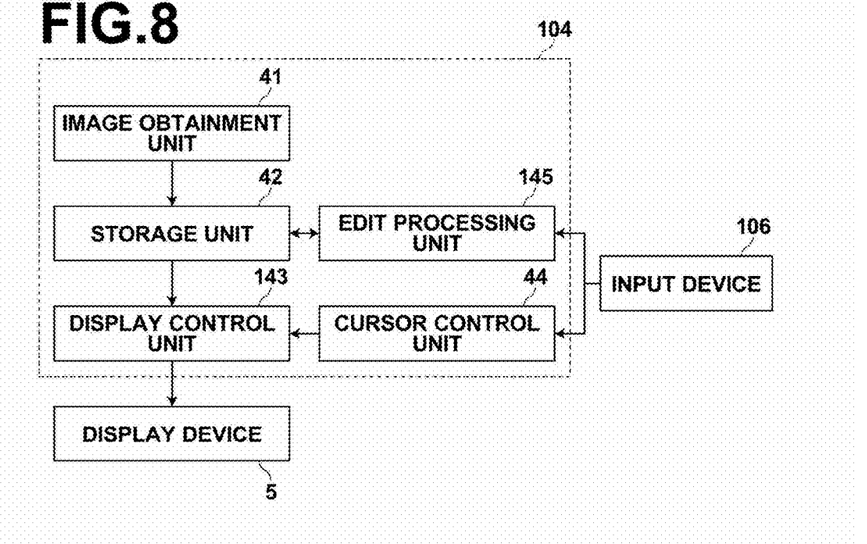
FIG. 8 is a block diagram illustrating functions installed in an image display apparatus illustrated in FIG. 7.

Next, a second embodiment of the present disclosure will be described with reference to drawings. FIG. 7 is a schematic block diagram illustrating the configuration of an image processing system including the second embodiment of the present disclosure. FIG. 8 is a functional block diagram illustrating the function of an image display apparatus 103 according to the second embodiment of the present disclosure. This embodiment differs from the aforementioned first embodiment only in that configuration for performing edit processing of changing image information about the three-dimensional image or information related to each voxel of the three-dimensional image (for example, information representing whether each of the voxels is included in a region of interest or the like) other than the image information is further provided. Therefore, in the following descriptions, the different point will be mainly explained, and regarding the same configuration as the first embodiment, the same numbers will be assigned, and explanation will be omitted.

The input device 106 corresponds to the operation receiving unit of the present disclosure. The input device 106 receives a user input giving an instruction to move cursor C, an instruction to execute edit processing or the like. In the embodiment of the present disclosure, the input device 106 is assumed to include both of a mouse and a keyboard, and to receive a user input by movement of the mouse itself, as a user input giving an instruction to move cursor C based on a movement direction and a movement amount of the mouse, and to receive an operation of an arrow key (a button unit) on the keyboard, as a user input giving an instruction to move cursor C from the display image in which the cursor is currently located into another display image located in a direction indicated by the operated arrow key. Further, the input device 106 receives a click operation of the mouse, as a user input giving an instruction to add a predetermined partial region to a region of interest that has been set in the three-dimensional image. Further, the input device 106 receives an operation of clicking the mouse while a control key on the keyboard is pressed, as a user input giving an instruction to delete a predetermined partial region from the region of interest.

The display control unit 143 reads out, from the storage unit 42, the three-dimensional image an instruction of display of which has been given, and displays plural tomographic images of the three-dimensional image intersecting each other on a display screen of the display device 5. Further, when a region of interest has been set in the three-dimensional image, if a user input giving an instruction to further display the range of the set region of interest is received, the display control unit 143 displays the range of the region of interest in the plural tomographic images displayed on the display screen in such a manner that the range of the region of interest is visually recognizable.

Next, a case in which the display control unit 143 reads out, from the storage unit 42, a three-dimensional image obtained by imaging a kidney region, and an instruction of display of which has been given, and displays three tomographic images T11 through T13, which are orthogonal triaxial images of the three-dimensional image, in display areas D1 through D3 and volume rendering image V of the kidney generated from the three-dimensional image in display area D4 on the display screen including four display areas D1 through D4, as illustrated in FIG. 9, will be considered. The display control unit 143 further displays, in each of tomographic images T11 through T13, range E of the kidney region (a region of interest) in a different color or colors from the other region based on information about range E of the kidney region in the three-dimensional image that has been obtained in advance by image analysis or like. When this display is provided for a user, the user can check range E of the kidney region, and further give an instruction to edit range E of the kidney region by addition or deletion, if necessary.

The display control unit 143 displays cursor C at a position in one of tomographic images T11 through T13 corresponding to a three-dimensional position at which three tomographic images T11 through T13 intersect each other in the three-dimensional image. Further, the display control unit 143 displays application range S of edit processing in each of tomographic images T11 through T13 and volume rendering image V. Application range S of edit processing means a partial region of the three-dimensional image to be added to range E of the kidney region or deleted from range E of the kidney region based on a user input giving an instruction to perform edit. Here, application range S of edit processing is assumed to be a spherical region having a predetermined radius with its center located at a position in the three-dimensional image corresponding to a cursor position.

The input device 106 receives a user input of moving the mouse itself. Then, the cursor control unit 44 moves, in response to receipt of the user input, cursor C based on a movement direction and a movement amount of the mouse. Then, the display control unit 143 displays orthogonal triaxial images intersecting each other at a three-dimensional position in the three-dimensional image corresponding to the position of the moved cursor in display areas D1 through D3. In this case, the display of a tomographic image in at least one of display areas D1 through D3 is changed to another tomographic image at a different slice position.

Further, the input device 106 receives a click operation of the mouse. Then, an edit processing unit 145 adds, in response to receipt of the operation, the region of application range S to range E of the kidney region. Then, the display control unit 143 displays range E of the kidney region on which addition processing has been performed in each of tomographic images T11 through T13. For example, when a user performs a click operation of the mouse in the state illustrated in FIG. 9, and the region of application range S is added to range E of the kidney region, the display control unit 143 displays range E of the kidney region that has become larger by addition processing in each of tomographic images T11 through T13, as illustrated in FIG. 10.

Further, the input device 106 receives a click operation of the mouse while a control key on the keyboard is pressed. Then, the edit processing unit 145 deletes, in response to receipt of the operation, the region of application range S from range E of the kidney region. Then, the display control unit 143 displays range E of the kidney region on which deletion processing has been performed in each of tomographic images T11 through T13.

The edit processing unit 145 changes, in response to a user input giving an instruction to perform edit, image information about the three-dimensional image or information related to each voxel of the three-dimensional image (for example, information representing whether each of the voxels is included in a region of interest or the like) other than the image information. For example, the input device 106 receives a click operation of the mouse in the state illustrated in FIG. 9, and the edit processing unit 145 changes, in response to receipt of the operation, information whether a voxel is included in the kidney region with respect to at least a part of voxels in application range S of edit processing. The edit processing unit 145 changes the information so that all the information representing whether each of voxels in the application range S of the edit processing is included in the kidney region, and which is related to each of the voxels, becomes information representing that each of the voxels is included in the kidney region. The region of application range S is added to range E of the kidney region, as illustrated in FIG. 10, by changing information in this manner.

Further, the input device 106 receives a click operation of the mouse while the control key on the keyboard is pressed, and the edit processing unit 145 changes, in response to receipt of the operation, information whether a voxel is included in the kidney region with respect to at least a part of voxels in application range S of edit processing. The edit processing unit 145 changes the information so that all the information representing whether each of voxels in the application range S of the edit processing is included in the kidney region, and which is related to each of the voxels, becomes information representing that each of the voxels is not included in the kidney region. The region of application range S is deleted from range E of the kidney region that has been set in the three-dimensional image by changing information in this manner.

The cursor control unit 44 moves, in response to receipt of a user input giving an instruction to move cursor C at the input device 106, cursor C based on the instruction by the user input. As described above, the cursor control unit 44 moves, in response to receipt of the user input of moving the mouse itself at the input device 106, cursor C based on the movement direction and the movement amount of the mouse. Further, the cursor control unit 44 moves, in response to receipt of an operation of an arrow key (a button unit) on the keyboard at the input device 106, cursor C from the tomographic image in which cursor C is currently located into another tomographic image located in the direction indicated by the operated arrow key. At this time, the cursor control unit 44 moves cursor C to a two-dimensional position in a tomographic image in which cursor C will be located after movement, and the two-dimensional position corresponding to the three-dimensional position in the three-dimensional image corresponding to the two-dimensional position pointed by cursor C in the tomographic image in which cursor C was located before movement. In this case, the three-dimensional position corresponding to the position of the cursor in the three-dimensional image does not change. Therefore, the display of a tomographic image in none of display areas D1 through D3 is changed to another tomographic image at a different slice position.

Figure 11:
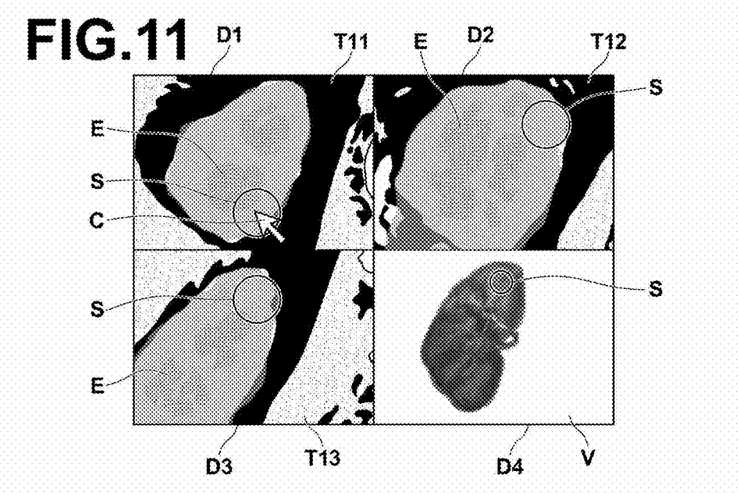
FIG. 11 is a diagram for explaining movement of a cursor by a button operation (No. 1)
Figure 12:
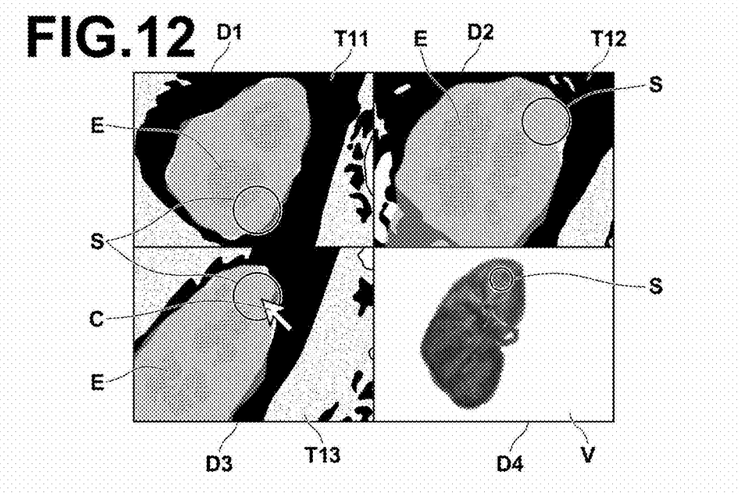
FIG. 12 is a diagram for explaining movement of a cursor by a button operation (No. 2)

For example, when a left arrow key on a keyboard is operated while cursor C is located in tomographic image T12, as illustrated in FIG. 10, the cursor control unit 44 moves cursor C to a two-dimensional position in tomographic image T11, as illustrated in FIG. 11. The two-dimensional position in tomographic image T11, which is located to the left of tomographic image T12, corresponds to the three-dimensional position in the three-dimensional image corresponding to the two-dimensional position pointed by cursor C in tomographic image T12, in which cursor C was located before movement. After then, when a down arrow key on the keyboard is further operated, the cursor control unit 44 moves cursor C to a two-dimensional position in tomographic image T13, as illustrated in FIG. 12. The two-dimensional position in tomographic image T13, which is located under tomographic image T11, corresponds to the three-dimensional position in the three-dimensional image corresponding to the two-dimensional position pointed by cursor C in tomographic image T11, in which cursor C was located before movement.

Figure 13:
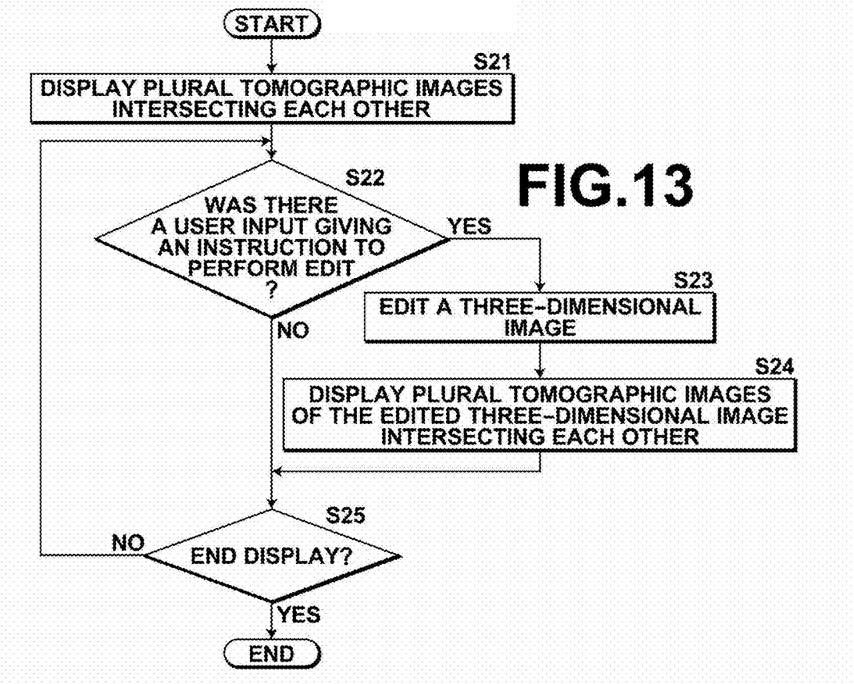
FIG. 13 is a flow chart showing a flow of processing related to edit performed by the image display apparatus.

Next, a flow of processing performed by the image display apparatus 103 will be described. FIG. 6 is a flow chart showing a flow of processing related to movement of cursor C from start to end of image display. FIG. 13 is a flow chart showing an example of processing related to edit from start to end of image display. In the image display apparatus 103, processing from starting display (S11, S21) till judging that an instruction to end display has been given (S16, S25: YES) in the two flow charts of FIGS. 6 and 13 are performed simultaneously or sequentially. Next, with reference to the flow chart illustrated in FIG. 13, a flow of processing related to edit unique to the embodiment of the present disclosure will be described.

As illustrated in FIG. 13, first, the image display apparatus 103 receives a user input giving an instruction to display a three-dimensional image, in which the three-dimensional image is specified. Then, the image obtainment unit 41 obtains the specified three-dimensional image from the imaging apparatus 1 or the image storage server 2. The display control unit 143 displays plural tomographic images intersecting each other of the three-dimensional image, an instruction of display of which has been given, on a display screen of the display device 5 (S21). Then, judgment is made as to whether there was a user input giving an instruction to perform edit at the input device 106 (S22). If it is judged that there was no user input giving an instruction to perform edit (S22: NO), judgment is further made as to whether there was an instruction to end display (S25). If it is judged that there was an instruction to end display (S25: YES), processing ends. In contrast, if it is judged that there was no instruction to end display (S25: NO), processing returns to step S22.

Meanwhile, if it is judged that there was a user input giving an instruction to perform edit in step S22 (S22: YES), the edit processing unit 145 changes, based on the instruction, image information about the three-dimensional image or information related to each voxel of the three-dimensional image (for example, information representing whether each of the voxels is included in a region of interest or the like) other than the image information. For example, if the user input received in step S22 is a click operation of the mouse, the edit processing unit 145 adds a predetermined partial region to the region of interest that has been set in the three-dimensional image. If the user input received in step S22 is a click operation of the mouse while the control key on the keyboard is pressed, the edit processing unit 145 deletes a predetermined partial region from the region of interest that has been set in the three-dimensional image. Specifically, the edit processing unit 145 changes, with respect to at least a part of voxels in the predetermined partial region to be added or deleted, information whether a voxel is included in the region of interest.

Then, the display control unit 143 displays a region of interest on which edit processing has been performed in each of plural tomographic images (S24), and goes to step S25. The display control unit 143 judges whether there was an instruction to end display (S25). If it is judged that there was no instruction to end display as described above (S25: NO), processing returns to step S22. If it is judged that there was an instruction to end display (S25: YES), processing ends.

As the image display apparatus 103 according to an embodiment of the present disclosure is configured as described above, the display control unit 143 displays a first tomographic image (tomographic image T12) of the three-dimensional image on the display screen, and also displays cursor C to be operated by a user in the displayed first tomographic image (tomographic image T12), and also displays at least one second tomographic image (tomographic images T11 and T13) intersecting the first tomographic image (tomographic image T12) at the three-dimensional position in the three-dimensional image corresponding to the two-dimensional position pointed by cursor C in the first tomographic image (tomographic image T12). Further, the input device 106 (operation receiving unit) receives a user input by a button operation (an operation of an arrow key on the keyboard) giving an instruction to move cursor C. Further, the cursor control unit 44 moves cursor C, only by a simple button operation, to a two-dimensional position in one of the at least one second tomographic images (tomographic image T11 or T13) corresponding to the three-dimensional position in the three-dimensional image corresponding to the two-dimensional position pointed by cursor C in the first tomographic image (tomographic image T12). Therefore, it is possible to perform operations, such as checking and modifying, continuously in another tomographic image. It is possible to more efficiently perform an operation of checking or modifying the three-dimensional image while moving cursor C back and forth between plural tomographic images of the three-dimensional image intersecting each other.

Further, the image display apparatus 103 according to an embodiment of the present disclosure is configured to include the edit processing unit 145 to perform edit processing of changing image information about the three-dimensional image or information related to each voxel of the three-dimensional image other than the image information. Therefore, the image display apparatus 103 can change, in response to a user input giving an instruction to perform edit, image information about a partial region (region of application range S of edit processing) in the three-dimensional image or information related to each voxel in the partial region other than the image information, by the edit processing unit 145. Here, the partial region includes the three-dimensional position in the three-dimensional image corresponding to the two-dimensional position pointed by cursor C in the first tomographic image or one of at least one second tomographic images (tomographic image T12 in FIG. 9) in which cursor C is displayed.

The aforementioned embodiment described, as an example, a case in which application range S of edit processing is a spherical region having a predetermined radius with its center located at a position in the three-dimensional image corresponding to a cursor position. Alternatively, application range S of edit processing may be a rectangular parallelepiped or polyhedral region having a predetermined size with its center located at a three-dimensional position in the three-dimensional image pointed by cursor C.

Further, the aforementioned embodiment described a case in which a region of interest that has been set in the three-dimensional image is displayed in a different color or colors from the other region, as an example of a mode of displaying the region of interest in a visually recognizable manner. Alternatively, the region of interest may be displayed in a visually recognizable manner by using a different display mode, such as displaying a surrounding line around the region of interest.

The aforementioned embodiment described a case in which the input device 106 receives a click operation of the mouse, as a user input giving an instruction to add a predetermined partial region to the region of interest, and receives a click operation of the mouse while a control key on the keyboard is pressed, as a user input giving an instruction to delete a predetermined partial region from the region of interest. However, the operation is not limited to these operations. The input unit 106 may use two other arbitrary input operations excluding an input operation giving an instruction to move cursor C, and which are different from each other, by allocating them to a user input giving an instruction to add a predetermined partial region to the region of interest and a user input giving an instruction to delete a predetermined partial region from the region of interest.

Further, the aforementioned first and second embodiments described a case in which the input devices 6, 106 receive an arrow key (button unit) operation on the keyboard, as a user input giving an instruction to move cursor C from a display image in which cursor C is currently located into another display image located in the direction indicated by the operated arrow key. However, the operation is not limited to this operation. The input device 6, 106 may use another arbitrary button operation, such as a button operation of a left button or a right button of the mouse, a button (key) operation on the keyboard, and an operation of rolling a center button of the mouse (a wheel button) forward and backward, as a user input for moving cursor C to a position in another display image that three-dimensionally corresponds to the current position of cursor C (a button operation giving an instruction to move the cursor).

Further, the aforementioned first and second embodiments described a case in which the input devices 6, 106 receive a user input of moving the mouse itself, as a user input giving an instruction to move cursor C based on a movement direction and a movement amount of the mouse. However, the operation is not limited to this operation. Instead of the user input of moving the mouse itself, the input device 6, 106 may use other input operations, for example, such as up, down, left and right key operations on the keyboard and an operation of rotating a ball of a trackball mouse by hand, excluding the aforementioned "button operation giving an instruction to move the cursor", as a user input for moving cursor C in a predetermined direction by a predetermined amount.

Further, the aforementioned first and second embodiments described, as an example, a case in which the display control units 43, 143 display orthogonal triaxial images. The display control units 43, 143 should display at least two tomographic images of the three-dimensional image intersecting each other. It is not necessary that the at least two tomographic images intersect each other at a right angle.

What is claimed is:

1. An image display apparatus comprising:
a memory configured to store executable instructions; and
a processor configured to execute the executable instructions, which when executed by the processor cause the processor to perform the following functions:
display a first tomographic image of a three-dimensional image on a display screen, also display a cursor to be operated by a user in the displayed first tomographic image, also display at least one second tomographic image intersecting the first tomographic image at a three-dimensional position in the three-dimensional image corresponding to a two-dimensional position pointed by the cursor in the first tomographic image, and also display a mark on a two dimensional position of the at least one second tomographic corresponding to the three dimensional position of the cursor,
receive a user input by a button operation giving an instruction to move the cursor from the first tomographic image to the at least one second tomographic image, and
move, in response to receipt of the user input by the button operation, the cursor to a two-dimensional position in one of the at least one second tomographic image corresponding to the three-dimensional position in the three-dimensional image corresponding to the two-dimensional position pointed by the cursor in the first tomographic image.

2. The image display apparatus, as defined in claim 1, wherein the processor further functions to change, in response to a user input giving an instruction to perform edit, image information about a partial region of the three-dimensional image including the three-dimensional position in the three-dimensional image corresponding to the two-dimensional position pointed by the cursor in the first tomographic image or one of the at least one second tomographic image in which the cursor is displayed or information related to each of voxels in the partial region other than the image information.

3. The image display apparatus, as defined in claim 2, wherein when a region of interest has been set in the three-dimensional image, the processor further functions to display the range of the set region of interest in the first tomographic image and the at least one second tomographic image displayed on the display screen in a visually recognizable manner, and
change, in response to the user input giving an instruction to perform edit, information that is related to each of the voxels in the partial region and represents whether each of the voxels in the partial region is included in the region of interest.

4. The image display apparatus, as defined in claim 1, wherein the processor further functions to display a plurality of the second tomographic images,
   receive at least two different button operations, and
   determine, based on which of the at least two different button operation has been performed, one of the plurality of the second tomographic images into which the cursor is moved.

5. The image display apparatus, as defined in claim 2, wherein the processor further functions to display a plurality of two second tomographic images,
   receive at least two different button operations, and
   determine, based on which of the at least two different button operation has been performed, one of the plurality of two second tomographic images into which the cursor is moved.

6. The image display apparatus, as defined in claim 3, wherein the processor further functions to display a plurality of two second tomographic images,
   receive at least two different button operations, and
   determine, based on which of the at least two different button operation has been performed, one of the plurality of two second tomographic images into which the cursor is moved.

7. An image display method comprising the steps of:
   displaying a first tomographic image of a three-dimensional image on a display screen, also displaying a cursor to be operated by a user in the displayed first tomographic image, also displaying at least one second tomographic image intersecting the first tomographic image at a three-dimensional position in the three-dimensional image corresponding to a two-dimensional position pointed by the cursor in the first tomographic image, and also displaying a mark on a two dimensional position of the at least one second tomographic image corresponding to the three dimensional position of the cursor;
   receiving a user input by a button operation giving an instruction to move the cursor from the first tomographic image to the at least one second tomographic image; and
   moving, in response to receipt of the user input by the button operation, the cursor to a two-dimensional position in one of the at least one second tomographic image corresponding to the three-dimensional position in the three-dimensional image corresponding to the two-dimensional position pointed by the cursor in the first tomographic image.

8. The image display method, as defined in claim 7, the method further comprising the steps of:
   changing, in response to a user input giving an instruction to perform edit, image information about a partial region of the three-dimensional image including the three-dimensional position in the three-dimensional image corresponding to the two-dimensional position pointed by the cursor in the first tomographic image or one of the at least one second tomographic image in which the cursor is displayed or information related to each of voxels in the partial region other than the image information; and
   displaying, on the display screen, a plurality of tomographic images of the three-dimensional image in which one of the image information and the information other than the image information has been changed, and the plurality of tomographic images intersecting each other at the three-dimensional position in the three-dimensional image corresponding to the two-dimensional position pointed by the cursor.

9. A non-transitory computer-readable recording medium having stored therein an image display program that causes a computer to perform:
   display a first tomographic image of a three-dimensional image on a display screen, also display a cursor to be operated by a user in the displayed first tomographic image, also display at least one second tomographic image intersecting the first tomographic image at a three-dimensional position in the three-dimensional image corresponding to a two-dimensional position pointed by the cursor in the first tomographic image, and also display a mark on a two dimensional position of the at least one second tomographic image corresponding to the three dimensional position of the cursor;
   receive a user input by a button operation giving an instruction to move the cursor from the first tomographic image to the at least one second tomographic image; and
   move, in response to receipt of the user input by the button operation, the cursor to a two-dimensional position in one of the at least one second tomographic image corresponding to the three-dimensional position in the three-dimensional image corresponding to the two-dimensional position pointed by the cursor in the first tomographic image.

10. The non-transitory computer-readable recording medium having stored therein the image display program, as defined in claim 9, the program causing a computer to further perform:
    change, in response to a user input giving an instruction to perform edit, image information about a partial region of the three-dimensional image including a three-dimensional position in the three-dimensional image corresponding to the two-dimensional position pointed by the cursor in the first tomographic image or one of the at least one second tomographic image in which the cursor is displayed or information related to each of voxels in the partial region other than the image information.

* * * * *